United States Patent [19]

Surmatis

[11] 4,005,031
[45] Jan. 25, 1977

[54] NICKEL PEROXIDE OXIDIZING AGENT

[75] Inventor: Joseph Donald Surmatis, West Caldwell, N.J.

[73] Assignee: Hoffmann-La Roche Inc., Nutley, N.J.

[22] Filed: Feb. 19, 1976

[21] Appl. No.: 659,459

Related U.S. Application Data

[63] Continuation of Ser. No. 350,281, April 11, 1973.

[52] U.S. Cl. ............................. 252/186; 252/444; 252/447; 252/472; 252/531; 260/285; 260/524 N; 260/603 C

[51] Int. Cl.² ..................... C07B 3/00; C01B 15/04

[58] Field of Search .......... 252/472, 444, 447, 186, 252/531; 260/524 N, 285, 603 C

[56] References Cited

UNITED STATES PATENTS

| | | | |
|---|---|---|---|
| 2,045,054 | 7/1962 | Holm et al. | 252/447 |
| 2,767,160 | 10/1956 | Field et al. | 252/447 X |
| 3,192,258 | 6/1965 | Nakagawa et al. | 252/531 |
| 3,226,390 | 12/1965 | Nakagawa | 252/472 |
| 3,502,714 | 3/1970 | Nakagawa et al. | 252/472 X |
| 3,533,766 | 10/1970 | Gignier et al. | 252/472 X |
| 3,637,529 | 1/1972 | Van Beck et al. | 252/472 X |
| 3,663,166 | 5/1972 | Weise et al. | 252/447 X |
| 3,736,266 | 5/1973 | Schrage | 252/447 |
| 3,836,481 | 9/1974 | Kajimoto et al. | 252/447 X |

*Primary Examiner*—Richard E. Schafer
*Attorney, Agent, or Firm*—Samuel L. Welt; Bernard S. Leon; Richard A. Gaither

[57] ABSTRACT

Nickel peroxide on a fine, free-flowing carrier, which is formed by treating nickel oxide, deposited on the carrier, with an alkali hypohalite or alkali persulfate in an aqueous alkaline medium, and its use for selectively oxidizing an unsaturated alcohol to the corresponding carbonyl compound.

13 Claims, No Drawings

NICKEL PEROXIDE OXIDIZING AGENT

This is a continuation, of application Ser. No. 350,281 filed Apr. 11, 1973, entitled IMPROVED NICKEL PEROXIDE OXIDIZING AGENT.

BACKGROUND OF THE INVENTION

Nickel peroxide oxidizing agents have been generally described in U.S. Pat. No. 3,226,390 of Nakagawa et al. In this patent, the nickel peroxide formed by treating a nickel salt with an alkali hypohalite or persulfate has been disclosed as being particularly useful for oxidizing an unsaturated alcohol to the corresponding carbonyl compound. For example, it has been reported by Nakagawa et al. that vitamin A alcohol was oxidized with their nickel peroxide to vitamin A aldehyde under laboratory conditions in yields of 79%.

Problems have been encountered however in preparing and using nickel peroxide oxidizing agents outside of the laboratory. Nickel peroxide oxidizing agents have been found, for example, when prepared in bulk, by treating a nickel salt with an alkali hypohalite or persulfate, to coagulate on drying into impractically large aggregates. In this regard, it has been found that the consistency and selectivity of oxidations with nickel peroxide depend to a large extent upon using a fine and uniform nickel peroxide powder. As a result, the commercial preparation of efficient and selective nickel peroxide oxidizing agents has heretofore involved costly and time consuming operations to convert the nickel peroxide aggregates, as formed, to a suitable, fine, free-flowing form.

Furthermore, large scale oxidations utilizing heretofore available nickel peroxide oxidizing agents, formed by treating nickel salts with an alkali hypohalite or persulfate, have been difficult to control. Over-oxidation of unsaturated alcohol starting materials has been a frequently encountered problem. This has resulted, for example, in the formation of relatively large amounts of acids and other by-products, rather than carbonyl compounds, from the oxidation of unsaturated alcohols. Yields have fluctuated widely and have been generally inferior to the yields obtained in the laboratory.

There has been a need therefore for an improved nickel peroxide oxidizing agent which provides consistently high yields and which does not require costly treatment to convert it to a suitably fine, free-flowing form.

SUMMARY OF THE INVENTION

In accordance with this invention, an improved nickel peroxide oxidizing agent is provided by: treating nickel oxide, deposited on a carrier, with an alkali hypohalite or alkali persulfate in an aqueous alkaline medium.

By this invention, an improved nickel peroxide oxidizing agent is obtained which can be directly utilized for selectively oxidizing an unsaturated alcohol to the corresponding carbonyl compound in high yields. Also by this invention, a nickel peroxide oxidizing agent is obtained as a uniform, free-flowing solid which does not require further operations to make it effective as an oxidizing agent.

DETAILED DESCRIPTION OF THE INVENTION

The improved nickel peroxide oxidizing agent in accordance with this invention is obtained by first depositing nickel oxide on a fine, free-flowing carrier, and then treating the nickel oxide deposited on the carrier with an alkali hypohalite or alkali persulfate in an aqueous alkaline medium.

As used throughout this application, the term "nickel oxide" includes nickel hydroxide, nickel monoxide (NiO), nickel sesquioxide ($Ni_2O_3$) and nickelic tetraoxide ($Ni_3O_4$) and mixtures of two or more of the foregoing.

As also used throughout this application, the term "carrier" comprehends any conventional, inert carrier material which can be suitably formed into fine, free-flowing particles. Among the carrier materials which can be suitably utilized are included finely divided carbon, silica gel, alumina, clay and pumice. The preferred carriers have a particle size of about 65 to 325 mesh, especially a particle size of about 65 to 150 mesh. The preferred carrier material is graphite.

As further used throughout this application, the term "nickel carbonate" includes nickel carbonate ($NiCO_3$), basic nickel carbonate ($NiCO_3 \cdot Ni(OH)_2 \cdot 4H_4O$ and $2NiCO_3 \cdot 3Ni(OH)_2 \cdot 4H_2O$) and mixture of two or more of the foregoing.

In accordance with this invention, the deposit of nickel oxide on the carrier can be carried out in any conventional manner. Preferably, the deposition is carried out by forming nickel oxide in situ in an aqueous medium containing the carrier. In this way, the nickel oxide, as is formed, will precipitate onto the surface of the carrier, thereby intimately coating the carrier with nickel oxide.

In depositing nickel oxide, formed in situ, on the carrier, it is prepared to form initially an aqueous mixture, in which is dissolved a water-soluble nickel salt and which also contains fine, free-flowing carrier. This aqueous mixture is then treated, preferably while being stirred, with an alkali to precipitate nickel oxide onto the carrier. In this preferred deposition of nickel oxide, any conventional, water-soluble salt of nickel can be utilized to form the aqueous mixture containing the water-soluble nickel salt. Among the water-soluble nickel salts which can be utilized are included nickel chloride, nickel sulfate, nickel acetate and nickel nitrate.

In carrying out the deposition of nickel oxide, the aqueous mixture, in which is dissolved a water-soluble nickel salt, can formed in a conventional manner by adding a water-soluble nickel salt to water. In forming this aqueous mixture, it is especially preferred that the water-soluble nickel salt be formed in situ from one of the cheap and abundant, water-insoluble nickel salts, particularly nickel carbonate. The water-soluble nickel salt can be formed in situ by adding water-soluble nickel salt to an aqueous acid solution. In accordance with this especially preferred procedure, any conventional acid which will convert a water-soluble nickel salt to a water-soluble nickel salt can be utilized. The preferred acids are the mineral acids, such as hydrochloric acid, sulfuric acid, nitric acid, and hydrobromic acid, and the lower alkanoic acids, such as formic acid and acetic acid. Also in this procedure, the amount of acid utilized is not critical, and any amount of acid sufficient to convert the water-insoluble nickel to a water-soluble nickel salt of the particular acid can be utilized. Preferably about 1 gram equivalent of acid is utilized per 1 gram equivalent of the water-insoluble nickel salt.

In depositing nickel oxide, formed in situ, on the carrier, the aqueous mixture, containing the water-soluble nickel salt and the carrier, is treated with an alkali. In this procedure, any conventional alkali can be utilized, such as the alkali metal, alkaline earth metal and ammonium hydroxides and carbonates. Th preferred alkalis for depositing nickel oxide are the alkali metal hydroxides and alkaline earth metal hydroxides, particularly sodium, potassium and calcium hydroxide. In this deposition procedure, the amount of alkali utilized is not critical, and any amount that will convert the water-soluble nickel salt to nickel oxide can be utilized. Preferably, 1 gram equivalent of alkali is utilized per 1 gram equivalent of nickel salt in the aqueous mixture. However, if desired, greater or lesser amounts of the alkali, relative to the nickel salt, can be employed.

Also in this deposition procedure, the amounts of nickel oxide and carrier are not critical, and from 1 to 10 parts by weight of each can be suitably utilized. Preferably, 2:3 to 3:2 parts by weight of each are utilized, with about equal parts by weight of nickel oxide and carrier being particularly preferred. Furthermore, in this deposition, temperature and pressure are not critical, and the deposition can be conveniently carried out at from about 0° C. to about 100° C. and at atmospheric pressure. Preferably, temperatures of about room temperature (about 20°–30° C.) are utilized.

By this deposition procedure, nickel oxide is deposited on the surface of the carrier substrate. The resulting nickel oxide on the carrier can be either isolated in a conventional manner or directly converted, without isolation, to a nickel peroxide oxidizing agent in the manner set forth below.

The nickel oxide on the carrier substrate, formed as above, then is oxidized to form a nickel peroxide oxidizing agent by treating it with an alkali hypohalite or alkali persulfate in an equeous alkaline medium. In this reaction, any conventional alkali hypohalite or alkali persulfate can be utilized such as the alkali metal and alkaline earth metal hypohalites and persulfates. Preferred in this reaction are the alkali metal hypohalites and persulfates, particularly sodium hypochlorite, potassium hypochlorite, sodium hypobromide, sodium persulfate and potassium persulfate. In this reaction, any conventional aqueous alkaline medium can be utilized, such as aqueous solutions containing the alkali set forth above in connection with the deposition reaction. Preferably, the alkaline medium is a solution of an alkali metal hydroxide or an alkaline earth metal hydroxide. In carrying out this reaction, the relative amounts of alkali hypohalite or alkali persulfate and of nickel oxide, deposited on the carrier, are not critical, and from 1 to 10 parts by weight of each can be conveniently utilized. Preferably, the hypohalite or persulfate is utilized in an amount in excess of that which is required to completely convert all of the nickel oxide to nickel peroxide. In this reaction, temperature and pressure are not critical and the reaction can be conveniently carried out at room temperature and atmospheric pressure. The nickel peroxide oxidizing agent which is formed can be separated from the aqueous reaction mixture by filtration and cleaned by repeated washings with water.

The resulting nickel peroxide on the fine, free-flowing carrier can be conveniently utilized for selectively oxidizing a wide variety of unsaturated alcohols. Among the unsaturated alcohols which can be oxidized in an improved fashion in accordance with this application are the allylic and benzylic alcohols disclosed in U.S. Pat. No. 3,226,390, including benzyl alcohol, 1-phenylethanol, cinnamyl alcohol, benzoin, benzohydrol, methyl benzyl alcohol, α-furfuryl alcohol, 2-buten-1-ol, allyl alcohol, geraniol, vitamin A alcohol, and codeine. In accordance with this invention, it is preferred to utilize the improved nickel peroxide oxidizing agent for the oxidation of vitamin A alcohols, such as trans-vitamin A alcohol and mixtures of cis- and trans-vitamin A alcohols.

Oxidizing with the nickel peroxide oxidizing agent of this invention can be carried out in an inert organic solvent. In this reaction, any conventional inert organic solvent which will not be oxidized by the nickel peroxide can be utilized. Among the solvents which can be utilized are the aliphatic hydrocarbons, such as heptane, and the petroleum ethers. In this reaction, temperature and pressure are not critical, and the reaction can be suitably carried out at room temperature and atmospheric pressure. In this reaction, the ratio of unsaturated alcohol to oxidizing agent is not critical, and the ratio of oxidizing agent to alcohol can suitably be between about 10:1 to 1:10 parts by weight. However, the amount of oxidizing agent to be used for a particular unsaturated alcohol can be selected in a conventional manner in order to achieve complete oxidation of the alcohol. Preferably, at least about 1150 grams of the nickel peroxide oxidizing agent is utilized per gram mole of the unsaturated alcohol.

The spent oxidizing agent can be regenerated by treating it with an alkali hypohalite or alkali persulfate in an aqueous alkaline medium. This regeneration can be carried out in a conventional manner, such as in accordance with the procedure set forth above for treating the nickel oxide deposited on the carrier with an alkali hypohalite or alkali persulfate.

By the process of this invention, an improved nickel peroxide oxidizing agent can be produced, which can be utilized directly in oxidizing unsaturated alcohols. Also by the process of this invention, yields of at least about 80% of an unsaturated carbonyl compound can be consistently obtained from the corresponding unsaturated alcohol. Further by the process of this invention, high yields of vitamin A aldehydes, particularly of cis-vitamin A aldehydes, can be obtained conveniently from the corresponding vitamin A alcohol using only about the minimum, stoichiometric amount of oxidizing agent needed to completely oxidize the alcohol.

The examples which follow further illustrate the process of this invention. The graphite powder utilized had a size of 65–325 mesh. Percent (%) is percent by weight.

EXAMPLE 1

Preparation of Nickel Peroxide on Graphite Oxidizing Agent 752 g. of nickel carbonate hydrate, $NiCO_3 \cdot 2Ni(OH)_2 \cdot 4H_2O$, was dissolved in 3,750 ml. of 18% hydrochloric acid. Graphite powder (752 g.) was added to the solution, and the suspension was stirred for 30 min. 2000 ml. of aqueous sodium hydroxide (25%) was dropped into the stirred suspension over a period of 2 hr. at 25–35 C. The stirring was continued for an additional hour, the solid product was filtered by suction and washed with water on the filter, and the product was partially dried on the filter. The product was nickel oxide on graphite.

7,500 ml. of aqueous 16% sodium hypochlorite solution and 1,250 ml. of aqueous (50%) sodium hydroxide solution were placed in a 12 liter flask, and the nickel oxide on graphite, prepared above, was added slowly with stirring at 22°-26° C. One hour was required for the addition. Stirring was continued for an additional hour. The black solid obtained was filtered and washed repeatedly with water until the wash water had a pH of 8. The product then was dried at room temperature on a centrifuge. The product was a nickel peroxide on graphite oxidizing agent weighing 1,400 g., that was used in Examples 2-5, which follow.

EXAMPLE 2

The Oxidation of Trans-Vitamin A Alcohol

Trans-vitamin A alcohol (20 g.) having a purity of 95% was dissolved in 180 ml. of heptane. 60 g. of the nickel peroxide on graphite oxidizing agent was added in two equal portions over a period of 1 hour while the reaction was stirred under an atmosphere of nitrogen. The stirring was continued for an additional 2 hrs., and the spent oxidizing agent was filtered and washed with additional heptane. On removal of the solvent under vacuum, there was obtained 20 g. of trans-vitamin A aldehyde; absorption max. 370m$\mu$ ($E_1$ cm$^{1\%}$ = 1305) in cyclohexane. Yield was 82.4% based on U.V. spectrum assay.

EXAMPLE 3

The Oxidation of Cis- and Trans-Vitamin A Alcohol 23 g. of a crude, syrupy material, produced in accordance with the first paragraph of Example 1 of U.S. Pat. No. 3,441,623 and having an assay of approximately 40% vitamin A alcohol (70% cis-vitamin A and 30% trans-vitamin A) and 60% polyene by-products, was dissolved in 180 ml. of heptane. 69 g. of nickel peroxide on graphite oxidizing reagent then was added in two equal portions over a period of 1 hour. The stirring was continued for 2 additional hours under an atmosphere of nitrogen. The spent oxidizing agent was filtered off and washed with additional heptane. On removal of the solvent under vacuum, there was obtained 20.2 g. of crude vitamin A aldehyde; absorption max. at 350 and 367 m$\mu$ in cyclohexane. Yield was 80% based on U.V. spectrum assay, of cis- and trans-vitamin A aldehyde.

EXAMPLE 4

The oxidation of Cis- and Trans-Vitamin A Alcohol 20 g. of a crude syrup, produced in accordance with the first paragraph of Example 1 of U.S. Pat. No. 3,441,623 and having an assay of approximately 35% vitamin A alcohol (70% trans-vitamin A and 30% cis-vitamin A) and 65% polyene by-products, was dissolved in 180 ml. of heptane. 60 g. of nickel peroxide on graphite oxidizing agent then was added in two portions over a period of 1 hour, and the stirring then was continued for an additional 2 hours. The spent oxidizing was removed by filtration and washed with additional heptane on the filter. The solvent was removed by distillation to yield 19.5 g. of crude vitamin A aldehyde; absorption max. 368 m$\mu$ ($E_1$ $_{cm}$$^{1\%}$ = 440). Yield was, based on U.V. spectrum assay, about 74% cis- and trans-vitamin A aldehyde.

EXAMPLE 5

The Regeneration of the Nickel Peroxide on Graphite Oxidizing Agent 1435 g. spent oxidizing reagent was stirred in water at 50° C., filtered, and washed repeatedly with warm water until the filtrate was almost colorless. The filter cake was sucked as dry as possible in the filter, and then it was added to an aqueous solution which was made up of 7,500 ml. of aqueous 16% sodium hypochlorite and 1,200 ml. of aqueous 50% sodium hydroxide. The addition was carried out at 20°-25° over a period of 1 hr. The black slurry was stirred for an additional hour and filtered. The filtered solid was washed with water until the wash water had a pH of 8. The product then was dried on a centrifuge at room temperature (22° C.). 1,420 g. of nickel peroxide on graphite oxidizing agent was obtained.

EXAMPLE 6

Preparation of the Nickel Peroxide on Graphite 752 g. of nickel carbonate hydrate was placed in a 12 liter flask containing 3 liters of water in 870 ml. of concentrated hydrochloric acid was added to the flask to dissolve the nickel salt. 752 g. of graphite powder was added to the solution, and the suspension was stirred for 30 minutes, 1,000 ml. of 50% aqueous sodium hydroxide was dropped into the stirred suspension over a period of 2 hr. at 25°-35° C. The stirring was continued for an additional hour, and 4,000 ml. of aqueous 16% sodium hypochlorite was slowly added at 22°-26° C. One hour was required for the addition. Stirring was continued for an additional hour. The black solid which was obtained was filtered and washed repeatedly with water until the wash water had a pH of 8.0-8.5. The product obtained was dried at room temperature in a centrifuge, to yield 1405 g. of nickel peroxide on graphite oxidizing agent, that was used in Example 7, which follows.

EXAMPLE 7

The Oxidation of Geraniol 77 g. of geraniol, with an assay of 89.8%, by gas chromatography, was dissolved in 1,000 ml. of heptane and oxidized with 300 g. of nickel peroxide on graphite agent in 5 hrs. at 25°-40° C. The spent oxidizing agent was filtered and washed with additional heptane. On removal of the solvent under vacuum, there was obtained 72.6 g. (94.3% weight yield) of crude citral with an assay of 94.4%. The yield was 89%.

I claim:
1. A process for preparing nickel peroxide oxidizing agent, comprising: treating nickel oxide, deposited on fine, free-flowing graphite, with an alkali hypohalite or alkali persulfate in an aqueous alkaline medium.
2. The process of claim 1 wherein said nickel oxide is deposited on said graphite by forming an aqueous mixture, in which is dissolved a water-soluble nickel salt and which contains said graphite, and then treating said aqueous mixture with an alkali.
3. The process of claim 2 wherein said alkali is an alkali metal hydroxide or alkaline earth metal hydroxide.
4. The process of claim 2 wherein said aqueous mixture is formed by treating a water-insoluble nickel salt with an aqueous acid.

5. The process of claim 4 wherein said water-insoluble nickel salt is nickel carbonate.

6. The process of claim 4 wherein said acid is a mineral acid or a lower alkanoic acid.

7. The process of claim 1 wherein said graphite is of 65 to 325 mesh.

8. The oxidizing agent formed by the process of claim 1.

9. In a process for oxidizing unsaturated alcohols in an inert organic solvent medium with a nickel peroxide oxidizing agent prepared by treating nickel oxide with an alkali hypohalite or an alkali persulfate in an aqueous alkaline medium, the improvement which comprises: depositing said nickel oxide onto fine free-flowing graphite prior to said treatment.

10. The process of claim 9 wherein said nickel oxide is deposited on said graphite by forming an aqueous mixture, in which is dissolved a water-soluble nickel salt and which contains said graphite, and then treating said aqueous mixture with an alkali.

11. The process of claim 10 wherein said alkali is an alkali metal hydroxide or alkaline earth metal hydroxide.

12. The process of claim 11 wherein said water-soluble nickel salt is formed by treating a water-insoluble nickel salt with an aqueous acid.

13. The process of claim 12 wherein said water-insoluble nickel salt is nickel carbonate.

* * * * *